(12) United States Patent
Morotomi

(10) Patent No.: US 11,607,175 B2
(45) Date of Patent: Mar. 21, 2023

(54) TOILET SEAT DEVICE

(71) Applicant: TOTO LTD., Kitakyushu (JP)

(72) Inventor: Yo Morotomi, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 0 days.

(21) Appl. No.: 17/510,530

(22) Filed: Oct. 26, 2021

(65) Prior Publication Data

US 2022/0133238 A1    May 5, 2022

(30) Foreign Application Priority Data

Oct. 30, 2020 (JP) .............................. JP2020-182881

(51) Int. Cl.
*A61B 5/00* (2006.01)
*A47K 13/24* (2006.01)

(52) U.S. Cl.
CPC ............ *A61B 5/6887* (2013.01); *A47K 13/24* (2013.01)

(58) Field of Classification Search
CPC ............................ A61B 5/6887; A47K 13/24
See application file for complete search history.

(56) References Cited

U.S. PATENT DOCUMENTS

| 4,961,431 A | * | 10/1990 | Ikenaga | .................... | A61B 5/20 600/584 |
| 4,962,550 A | * | 10/1990 | Ikenaga | .................... | E03D 9/00 600/573 |
| 5,410,471 A | * | 4/1995 | Alyfuku | .................... | A61B 5/20 600/300 |
| 2006/0258915 A1 | * | 11/2006 | Ueda | ...................... | A47K 13/30 600/595 |
| 2008/0085217 A1 | * | 4/2008 | Mueller | .............. | G01N 21/643 422/83 |
| 2011/0071388 A1 | * | 3/2011 | Yared | ................... | A61B 6/0421 600/425 |
| 2016/0374619 A1 | * | 12/2016 | Borkholder | .......... | A61B 5/7246 600/301 |

(Continued)

FOREIGN PATENT DOCUMENTS

| CN | 208904018 U | 5/2019 |
| CN | 111629641 A | 9/2020 |

(Continued)

OTHER PUBLICATIONS

Decision to Grant for the corresponding Japanese Patent Application No. 2020-182881 dated on Aug. 18, 2022.

*Primary Examiner* — Christopher A Flory
(74) *Attorney, Agent, or Firm* — Pearne & Gordon LLP

(57) ABSTRACT

According to the embodiment, a toilet seat device includes a toilet seat and a biological sensor. The toilet seat that is formed of a resin material and includes a seating part on which a user is seated, and a bottom surface part facing the seating part. The biological sensor that is of an optical type, is positioned inside the toilet seat, and detects biological information of the user seated on the seating part. The seating part includes a thick portion and a thin portion. The thin portion is thinner than the thick portion. The biological sensor is located at a back surface side of the thin portion. The thick portion and the thin portion are formed as a continuous body. The thin portion has a thickness that can transmit irradiated light irradiated from the biological sensor and reflected light reflected from the user seated on the seating part.

9 Claims, 9 Drawing Sheets

(56) References Cited

U.S. PATENT DOCUMENTS

| | | | |
|---|---|---|---|
| 2017/0231442 A1* | 8/2017 | Tsujita | E03D 5/105 4/313 |
| 2018/0014781 A1* | 1/2018 | Clavelle | A61B 5/6824 |
| 2018/0092602 A1* | 4/2018 | Hall | A61B 5/02427 |
| 2020/0029907 A1* | 1/2020 | Kobayashi | A61B 5/6891 |
| 2020/0039382 A1* | 2/2020 | Ozawa | B60N 2/66 |
| 2020/0359855 A1 | 11/2020 | Isomura et al. | |
| 2020/0390367 A1* | 12/2020 | Hall | A61B 5/6891 |
| 2020/0390398 A1* | 12/2020 | Hall | A61B 8/00 |
| 2021/0045594 A1* | 2/2021 | Isomura | A47K 13/24 |
| 2021/0388594 A1* | 12/2021 | Hall | G01J 5/10 |

FOREIGN PATENT DOCUMENTS

| | | | |
|---|---|---|---|
| JP | 2008-293928 A | 12/2008 |
| JP | 2012-149485 A | 8/2012 |
| JP | 2015-148106 A | 8/2015 |
| JP | 2017-006183 A | 1/2017 |
| JP | 2019-027139 A | 2/2019 |
| JP | 2019-126382 A | 8/2019 |
| JP | 2020-039852 A | 3/2020 |

* cited by examiner

TOILET SEAT DEVICE

CROSS-REFERENCE TO RELATED APPLICATIONS

This application is based upon and claims the benefit of priority from Japanese Patent Application No. 2020-182881, filed on Oct. 30, 2020; the entire contents of which are incorporated herein by reference.

FIELD

Embodiments described herein relate generally to a toilet seat device.

BACKGROUND

There is a toilet seat device that can measure the pulse wave of a user seated on a toilet seat by using a pulse wave sensor located in the toilet seat (JP-A 2020-39852 (Kokai) and JP-A 2017-6183 (Kokai)).

The pulse wave sensor described in JP-A 2020-39852 (Kokai) detects a vibration due to the pulse wave of the user seated on the toilet seat. However, the pulse wave may not be able to detect with high accuracy because there is a possibility that such a pulse wave sensor may misdetect body movement of the user. On the other hand, a pulse wave sensor described in JP-A 2017-6183 (Kokai) measures a pulse wave by receiving light reflected by a blood vessel of the user seated on the toilet seat. However, the appearance of the toilet seat may be degraded because it is necessary to provide an opening and/or a sensor window in the seating part of the toilet seat for the pulse wave sensor.

SUMMARY

According to the embodiment, a toilet seat device includes a toilet seat and a biological sensor. The toilet seat that is formed of a resin material and includes a seating part on which a user is seated, and a bottom surface part facing the seating part. The biological sensor that is of an optical type, is positioned inside the toilet seat, and detects biological information of the user seated on the seating part. The seating part includes a thick portion and a thin portion. The thin portion is thinner than the thick portion. The biological sensor is located at a back surface side of the thin portion. The thick portion and the thin portion are formed as a continuous body. The thin portion has a thickness that can transmit irradiated light irradiated from the biological sensor and reflected light reflected from the user seated on the seating part.

DETAILED DESCRIPTION

Figure 1:
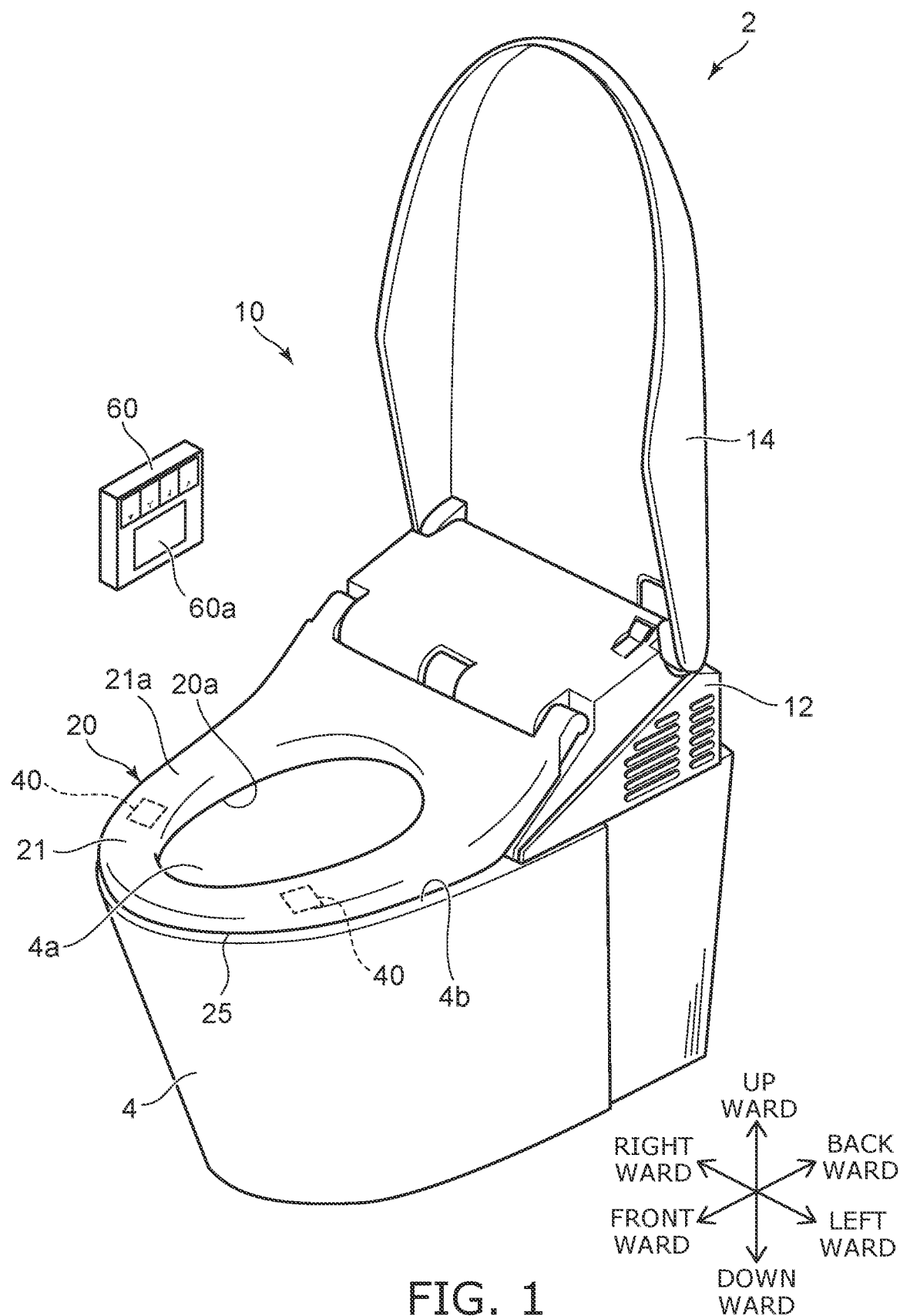
FIG. 1 is a perspective view showing a toilet device that includes a toilet seat device according to an embodiment of the invention.

An aspect of the invention is a toilet seat device that includes: a toilet seat that is formed of a resin material, includes a seating part on which a user is seated, and includes a bottom surface part facing the seating part; and a biological sensor that is of an optical type, is positioned inside the toilet seat, and detects biological information of the user seated on the seating part, wherein the seating part includes a thick portion and a thin portion, the thin portion is thinner than the thick portion, the biological sensor is located at a back surface side of the thin portion, the thick portion and the thin portion are formed as a continuous body, and the thin portion has a thickness that can transmit irradiated light irradiated from the biological sensor and reflected light reflected from the user seated on the seating part.

Exemplary embodiments will now be described with reference to the drawings. Similar components in the drawings are marked with like reference numerals; and a detailed description is omitted as appropriate.

FIG. 1 is a perspective view showing a toilet device that includes a toilet seat device according to an embodiment of the invention.

As shown in FIG. 1, the toilet device 2 includes a toilet 4 and the toilet seat device 10. The toilet 4 is a so-called sit-down flush toilet. The toilet 4 includes a concave bowl 4a that is recessed downward. The toilet 4 receives excrement of a user such as urine, feces, etc., in the bowl 4a. The toilet seat device 10 is mounted to the upper part of the toilet 4. The toilet seat device 10 may be integrally mounted to the toilet 4 or may be detachably mounted to the toilet 4.

Figure 2:
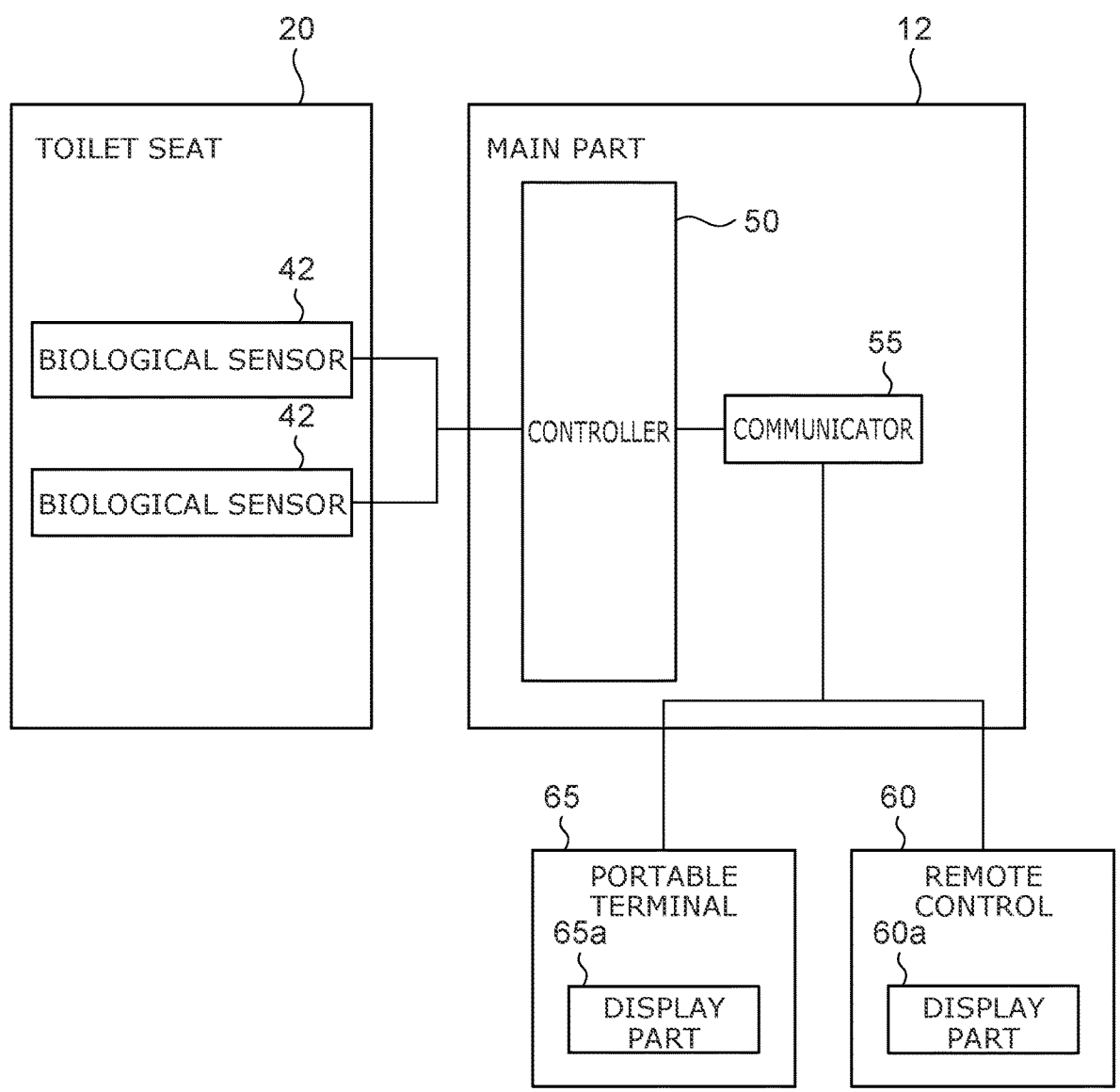
FIG. 2 is a block diagram showing a communication system of biological information control.

FIG. 2 is a block diagram showing a communication system of biological information control.

Figure 3:
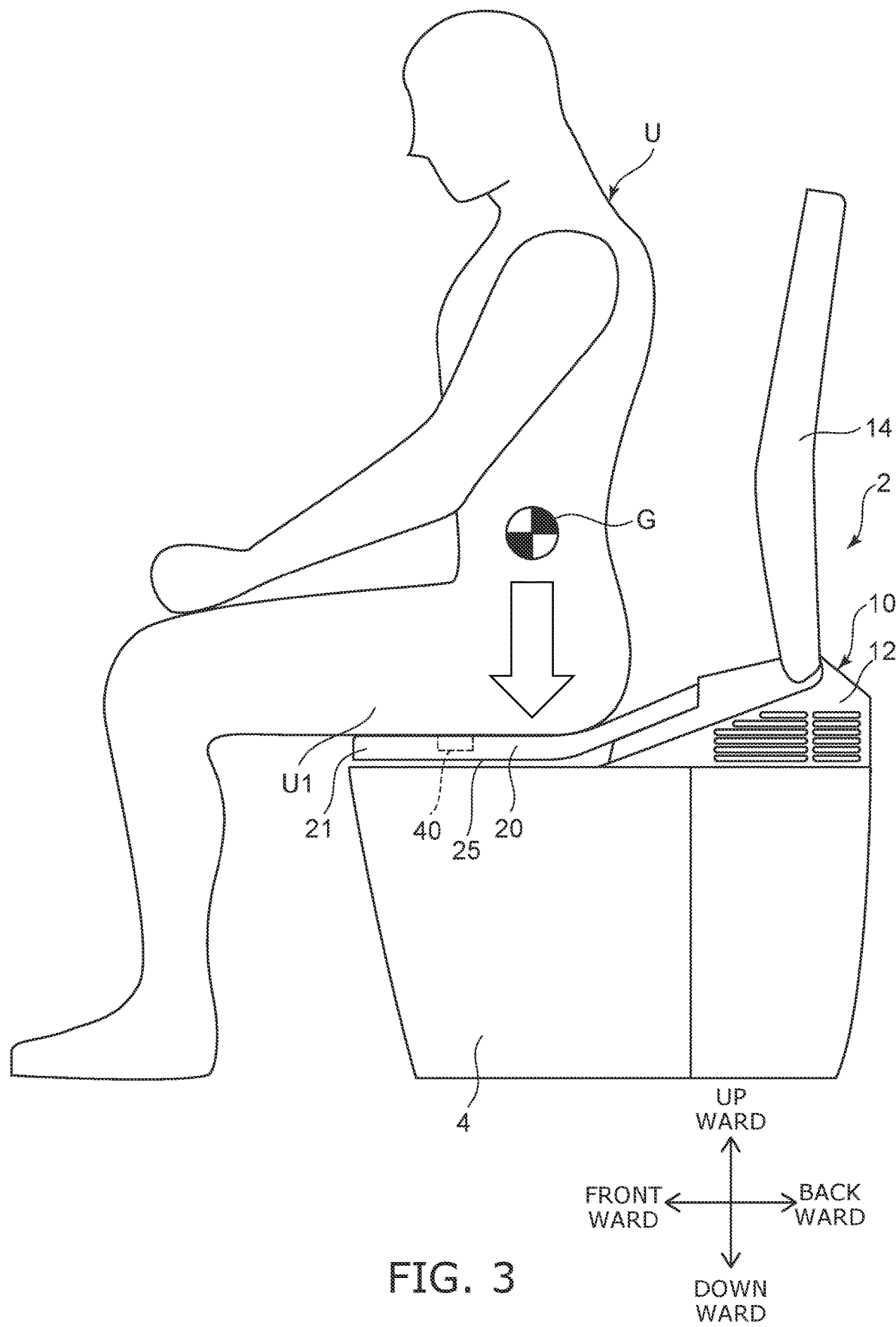
FIG. 3 is a side view showing the positional relationship between the biological sensor and the user seated on the toilet seat.

FIG. 3 is a side view showing the positional relationship between the biological sensor and the user seated on the toilet seat.

Figure 4:
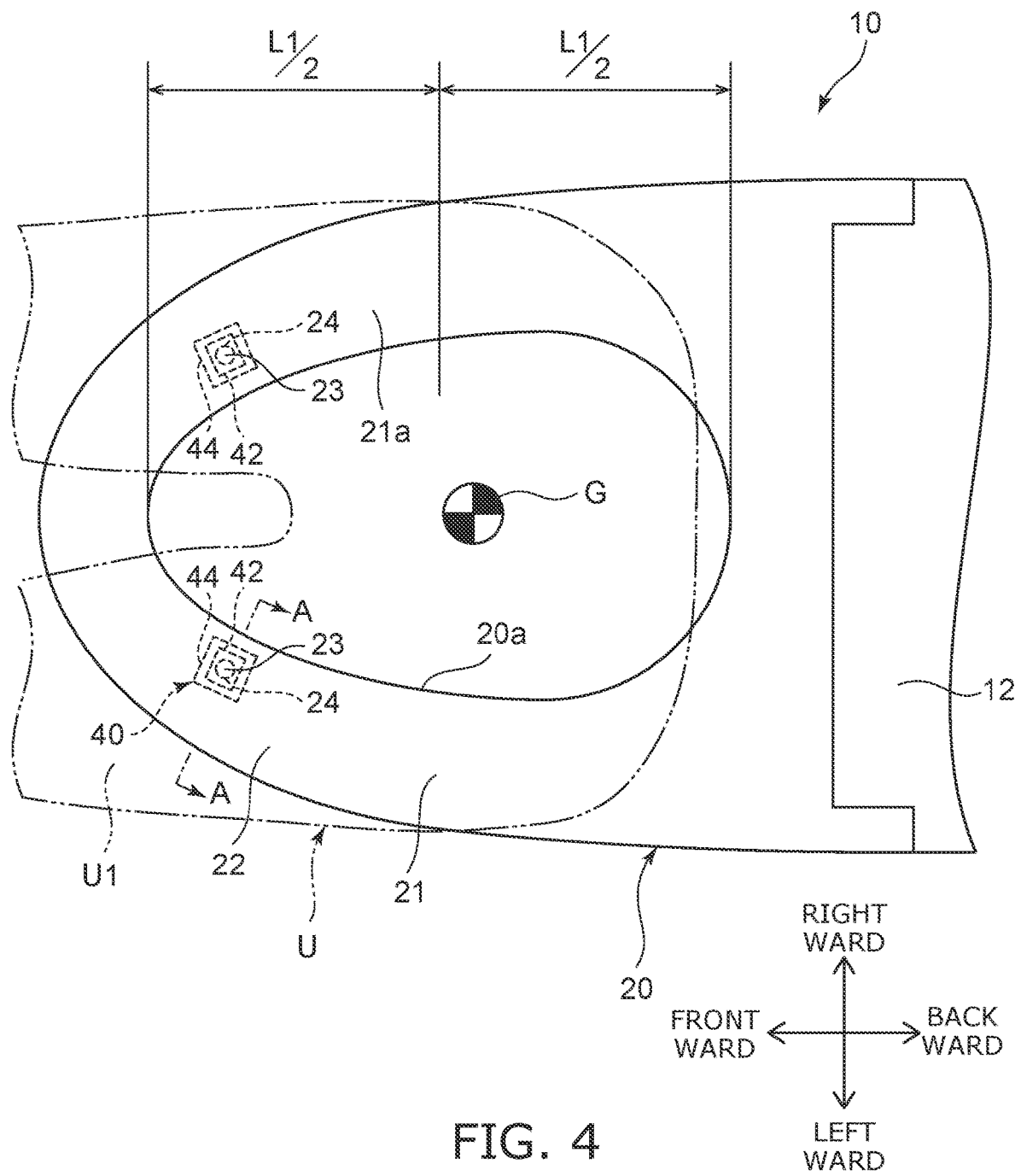
FIG. 4 is a plan view showing the positional relationship of the biological sensor.

FIG. 4 is a plan view showing the positional relationship of the biological sensor.

Figure 5:
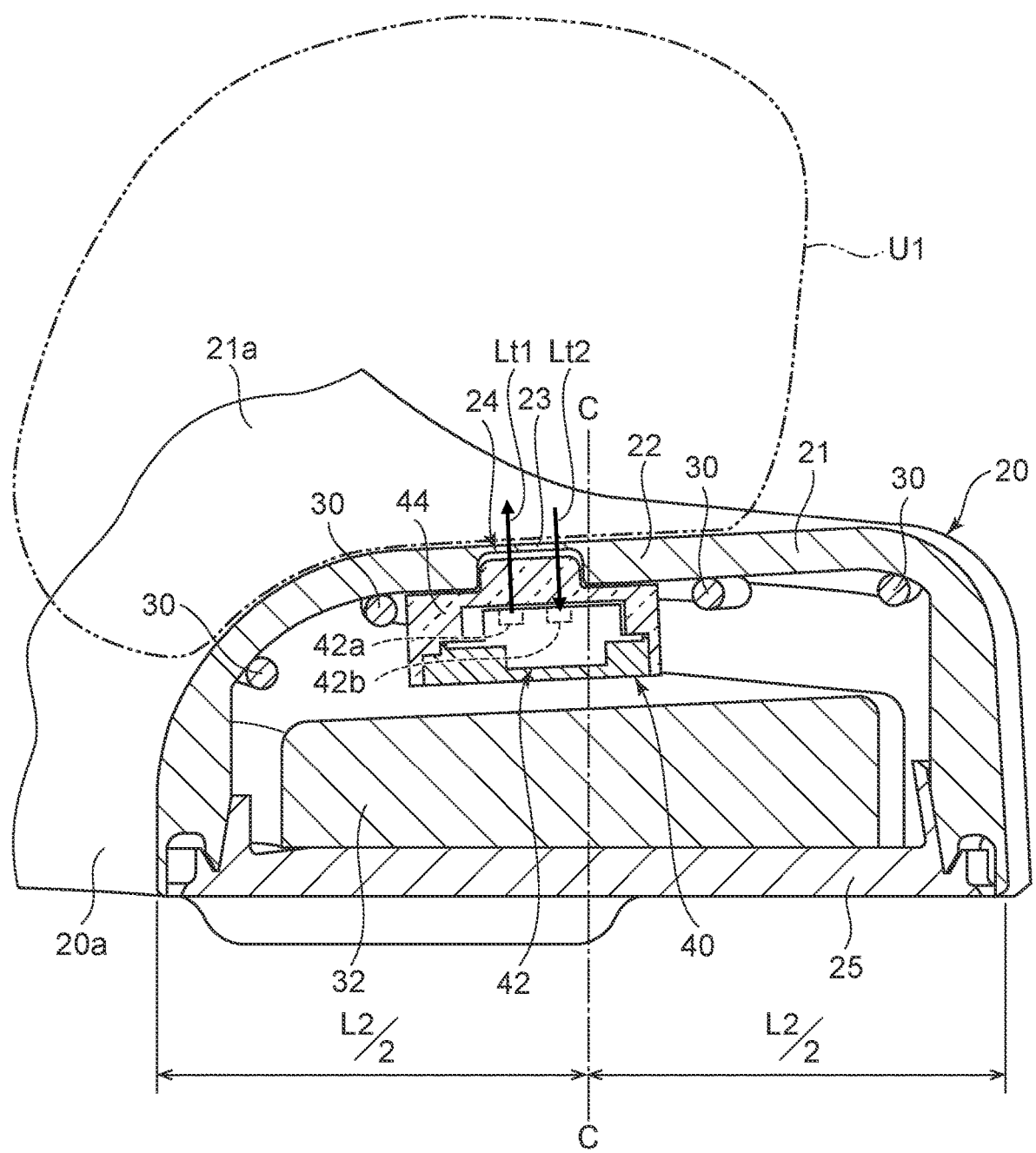
FIG. 5 is a cross-sectional view of the toilet seat, the reinforcing member, and the biological sensor of FIG. 4 when viewed from the arrow A-A-direction.

FIG. 5 is a cross-sectional view of the toilet seat, the reinforcing member, and the biological sensor of FIG. 4 when viewed from the arrow A-A-direction.

Figure 6:
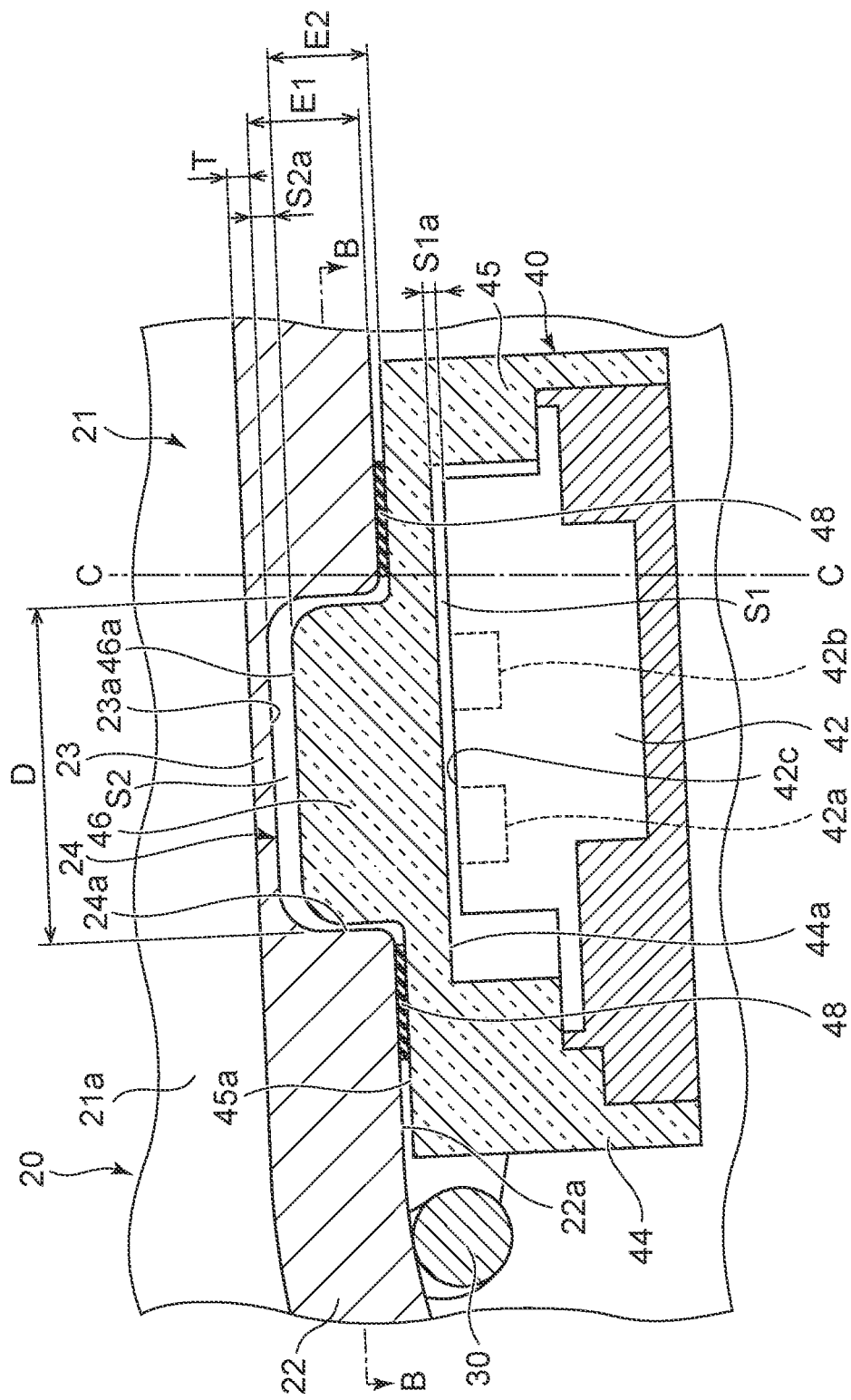
FIG. 6 is an enlarged cross-sectional view of the reinforcing member and the biological sensor of FIG. 5.

FIG. 6 is an enlarged cross-sectional view of the reinforcing member and the biological sensor of FIG. 5.

Figure 7:
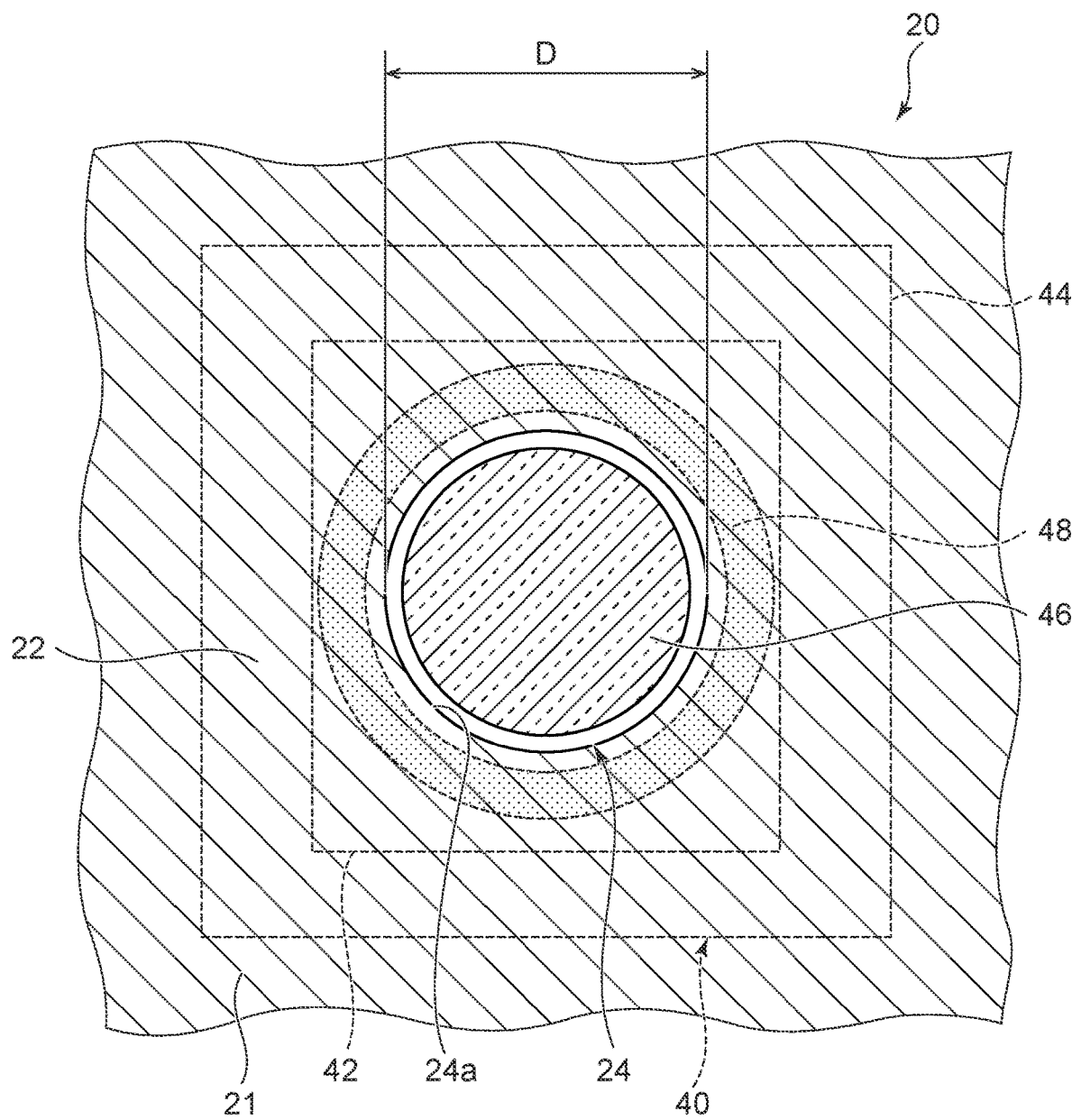
FIG. 7 is a cross-sectional view showing the toilet seat and the reinforcing member of FIG. 6 from the arrow B-B-direction.

FIG. 7 is a cross-sectional view showing the toilet seat and the reinforcing member of FIG. 6 from the arrow B-B-direction.

Figure 8:
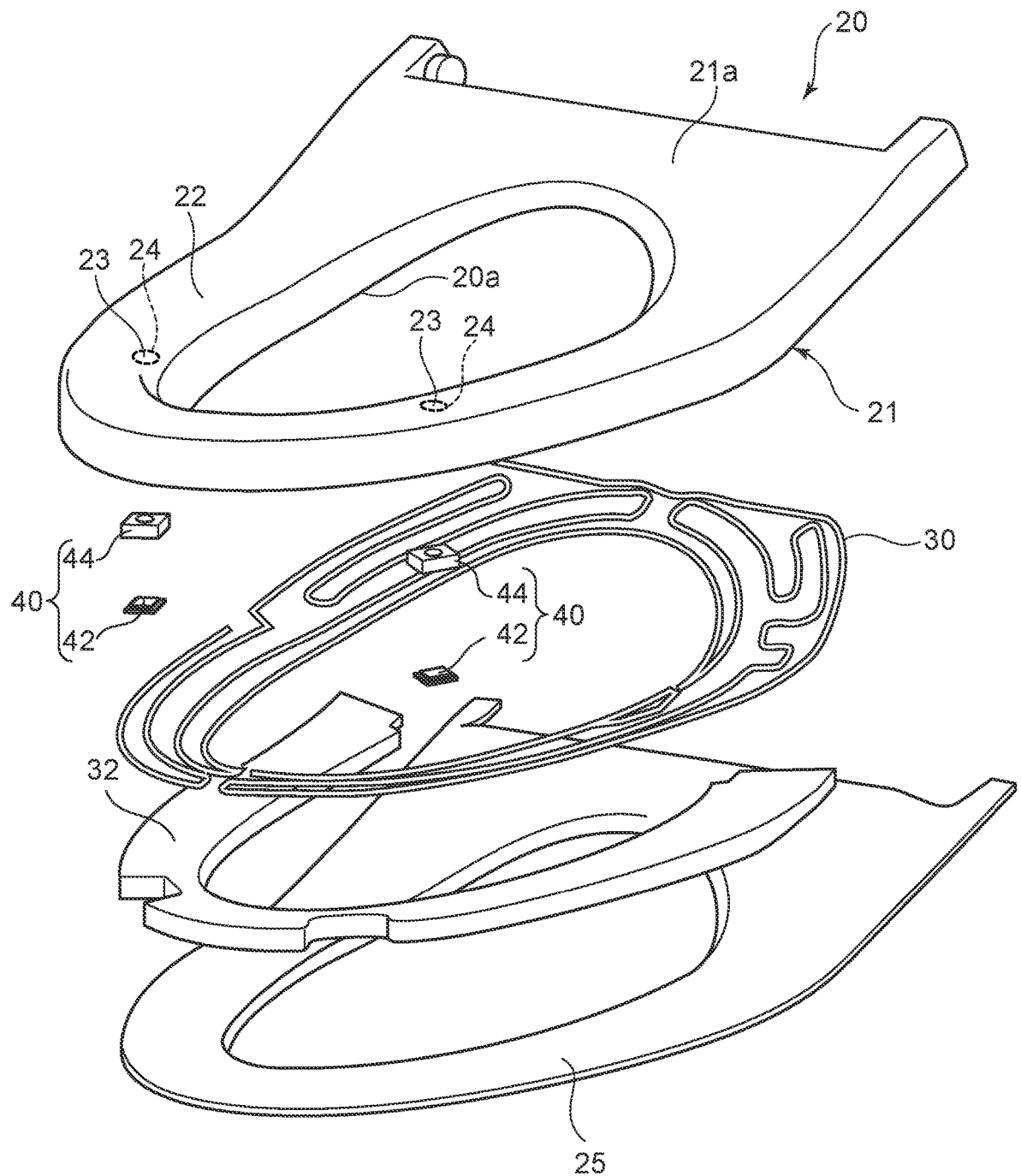
FIG. 8 is an exploded perspective view showing the toilet seat, insulation, a heater wire, the biological sensor, and the reinforcing member.

FIG. 8 is an exploded perspective view showing the toilet seat, insulation, a heater wire, the biological sensor, and the reinforcing member.

As shown in FIGS. 1 and 2, the toilet seat device 10 includes a toilet seat 20 and a biological sensor 42. The toilet seat device 10 also includes a main part 12 and a toilet lid 14. The toilet lid 14 is provided as necessary in the toilet seat device 10 and is omissible. The toilet seat 20 and the toilet lid 14 are pivotally supported to be rotatable with respect to the main part 12.

In this specification, "upward", "downward", "frontward", "backward", "leftward", and "rightward" each are directions when viewed by a user sitting on the toilet seat 20 with the user's back toward the open toilet lid 14.

The main part 12 of the toilet seat device 10 is positioned further backward than the bowl 4a of the toilet 4 and is mounted to an upper surface 4b of the toilet 4. Embedded as necessary inside the main part 12 are an opening/closing unit that controls the opening/closing operations of the toilet seat 20 and the toilet lid 14, a toilet seat heating unit that controls the temperature of the toilet seat 20, a washing unit that washes a human body private part, a deodorizing unit that decreases offensive-odor components, a controller 50 that comprehensively controls these operations, and a communicator 55 for communicating with a remote control 60 in the toilet room or the like.

The controller 50 is connected with the optical biological sensor 42 located inside the toilet seat 20. Detected values from biological information such as blood flow, a pulse wave, and the like of a user U seated on the toilet seat 20 are output by the biological sensor 42 to the controller 50. The controller 50 measures the pulse rate, the pulse rate variability, the blood flow, and the like of the pulse rate of the user U seated on the toilet seat 20 based on the detection result of the biological sensor 42.

Then, the measured values such as the pulse rate, etc., are transmitted by the controller 50 from the communicator 55 to a portable terminal 65 of the user and the remote control 60 for operating the toilet device 2. Wireless communication or wired communication may be performed between the communicator 55 and the remote control 60 and between the communicator 55 and the portable terminal 65. Then, the user U that is seated on the toilet seat 20 can check vital signs such as the pulse rate, etc., by using a display part 60a of the remote control 60 and/or a display part 65a of the portable terminal 65.

The toilet seat 20 is formed so that the outer edge is curved along the exterior shape of the toilet 4; and the toilet seat 20 is pivotally supported by the main part 12 to be rotatable. The toilet seat 20 is formed of an opaque resin material (e.g., polypropylene). The toilet seat 20 includes a seating part 21 on which the user U is seated, and a bottom surface part 25 that faces the seating part 21.

In the state in which the toilet seat 20 is placed on the upper surface 4b of the toilet 4, the seating part 21 is the upper surface part of the toilet seat 20, and is the part on which the user U is seated. In the state in which the toilet seat 20 is lowered, the bottom surface part 25 faces the upper surface 4b of the toilet 4 in the vertical direction. A biological unit 40, insulation 32, and a heater wire 30 that maintains the temperature of the seating part 21 are located inside the toilet seat 20. The heater wire 30 is located at the back surface of the seating part 21 and is controlled by the toilet seat heating unit located in the main part 12. The insulation 32 is positioned below the heater wire 30 and the biological unit 40 and is located in the bottom surface part 25.

The toilet seat 20 includes an opening 20a that extends through the bowl 4a. In the example as shown in FIG. 4, a so-called O-shaped toilet seat 20 is shown in which the opening 20a is formed in the central part of the toilet seat 20. The toilet seat 20 is not limited to O-shaped and may be U-shaped, etc. In other words, the shape of the toilet seat 20 when viewed from above in the state of use (the state in which the user U can be seated) is ring-shaped or U-shaped. The user U can excrete into the bowl 4a when sitting on the toilet seat 20.

As shown in FIGS. 5 and 6, the seating part 21 includes a thick portion 22 that is formed so that the thickness dimension is large, and a thin portion 23 that is formed to be thinner than the thick portion 22. The thick portion 22 and the thin portion 23 are formed as a continuous body in the seating part 21. Therefore, a joint is not formed between the thick portion 22 and the thin portion 23 in a front surface 21a of the seating part 21; therefore, degradation of the appearance of the toilet seat 20 can be suppressed; and penetration of water into the toilet seat 20 can be suppressed. The heater wire 30 that maintains the temperature of the seating part 21 is located at a back surface 22a of the thick portion 22. The biological unit 40 is located between the adjacent heater wires 30 at a back surface 23a side of the thin portion 23.

The thin portion 23 has a thickness T that can transmit irradiated light Lt1 irradiated from the biological sensor 42 and reflected light Lt2 reflected from the user U seated on the seating part 21. The thickness T is, i.e. thinner than the thickness at which the signal-to-noise ratio is greater than 0 dB for the irradiated and reflected light intensities. Furthermore, the thickness T is thicker than the thickness at which the thin portion 23 can be molded, and thick enough to deter breakage of the thin portion 23 in normal use. As shown in FIG. 6, the thickness T of the thin portion 23 is set according to the irradiated light Lt1 of the biological sensor 42, the intensity of the reflected light Lt2, the durability of the seating part 21, etc., and is, for example, about 0.5 mm to 1.0 mm.

A recessed portion 24 is provided in the back surface side of the seating part 21. The recessed portion 24 is recessed from the back surface 22a of the thick portion 22 toward the front surface 21a of the seating part 21. A reinforcing member 44 of the biological unit 40 is inserted into the recessed portion 24. The bottom portion of the recessed portion 24 is the thin portion 23 of the seating part 21. The recessed portion 24 includes a circumferential wall surface 24a that extends from the back surface 22a of the thick portion 22 toward the back surface 23a of the thin portion 23. In other words, the recessed portion 24 is a concave recess that includes the circumferential wall surface 24a and the back surface 23a of the thin portion 23 as the bottom surface.

Multiple (e.g., two) recessed portions 24 are formed in the seating part 21 at laterally-symmetric positions of the seating part 21. As shown in FIG. 4, the recessed portions 24 are positioned frontward of a center-of-gravity position G of the user U seated on the toilet seat 20. In other words, the recessed portions 24 are formed frontward of the center of a longitudinal-direction length L1 of the opening 20a of the toilet seat 20. Also, as shown in FIG. 5, at least a portion of each recessed portion 24 is further toward the opening 20a side of the toilet seat 20 than a centerline C-C of a lateral-direction width dimension L2 of the seating part 21.

The shape of the recessed portion 24 corresponds to a protrusion 46 of the reinforcing member 44 described below. In the example as shown in FIG. 7, the recessed portion 24 is circular when viewed in plan. In other words, the thin portion 23 that forms the bottom portion of the recessed portion 24 is circular when viewed in plan.

As shown in FIGS. 6 and 7, a maximum diameter D of the thin portion 23 (the recessed portion 24) is formed to be as small as possible within a range in which the biological sensor 42 can detect the biological information of the user U seated on the toilet seat 20. In other words, the maximum diameter D is set to a diametrical-direction dimension such that the light rays of the reflected light Lt2 and the irradiated light Lt1 of the biological sensor 42 can pass through the thin portion 23.

The maximum diameter D of the thin portion 23 is set to be, for example, not more than 12 mm (favorably not more than 8 mm). By setting the maximum diameter D of the thin portion 23 to be this small, the reduction of the rigidity of the toilet seat 20 can be suppressed. Also, even if the thin portion 23 is damaged, the user U can be prevented from inserting a finger, etc., into the recessed portion 24.

As shown in FIGS. 5 and 6, the protrusion 46 of the reinforcing member 44 is inserted into the recessed portion 24. A depth dimension E1 of the recessed portion 24 from the back surface 22a of the thick portion 22 to the back surface 23a of the thin portion 23 is greater than a protrusion dimension E2 of the protrusion 46 of the reinforcing member 44. Thereby, the reinforcing member 44 can contact the back surface 22a of the thick portion 22 when mounting the reinforcing member 44 to the seating part 21.

The biological unit 40 is positioned inside the toilet seat 20 and is located at the back surface 23a side of the thin portion 23 included in the seating part 21. Two biological units 40 are separated from each other in the lateral direction of the toilet seat 20. The biological unit 40 includes the reinforcing member 44 that reinforces the toilet seat 20, and the biological sensor 42 that is mounted to the reinforcing member 44 and detects the biological information of the user U seated on the toilet seat 20.

The biological sensor 42 is located at the back surface 23a side of the thin portion 23. In other words, the biological sensor 42 is positioned below the thin portion 23 in the state in which the toilet seat 20 is closed. The biological sensor 42 is mounted to the reinforcing member 44 described below.

The biological sensor 42 is an optical biological sensor that uses visible light and/or a laser to detect the blood flow of the user U seated on the toilet seat 20. Also, the biological sensor 42 is a reflective sensor that detects the reflected light Lt2 when the irradiated light Lt1 is irradiated toward a thigh portion U1 of the user U and is reflected by the blood flow of the user U. In the example, the biological sensor 42 includes a laser blood flow sensor that can use infrared to detect the flow rate change of red blood cells flowing through a blood vessel.

The biological sensor 42 that includes the blood flow sensor includes an irradiation part 42a that irradiates the irradiated light Lt1 of infrared, and a receiver 42b that receives the scattered light (the reflected light) of the red blood cells flowing through the blood vessel. The biological sensor 42 detects the Doppler-shifted frequency due to the red blood cells flowing through the blood vessel.

As shown in FIG. 6, the biological sensor 42 is mounted to the reinforcing member 44 to form a gap S1 between a front surface 42c of the biological sensor 42 and a back surface 44a of the reinforcing member 44. A dimension S1a of the gap S1 is set by considering the manufacturing tolerances of the biological sensor 42 and the reinforcing member 44. The dimension S1a of the gap S1 is less than a dimension S2a of a gap S2 between the back surface 23a of the thin portion 23 and a front surface 46a of the reinforcing member 44 described below (S1a<S2a). The attenuation of the reflected light Lt2 and the irradiated light Lt1 of the biological sensor 42 can be suppressed thereby.

As shown in FIG. 5, the biological sensor 42 irradiates the irradiated light Lt1 of infrared from the irradiation part 42a toward the blood vessel inside the thigh portion U1 of the user U via the thin portion 23 and the protrusion 46 of the reinforcing member 44. Then, the receiver 42b of the biological sensor 42 receives the reflected light Lt2 reflected from the user U. Thereby, the biological sensor 42 can non-invasively detect the biological information of the user U seated on the toilet seat 20. Then, the biological sensor 42 transmits the detection signal that is detected to the controller 50.

The reinforcing member 44 is located between the biological sensor 42 and the thin portion 23 of the seating part 21. The reinforcing member 44 is made of, for example, a transparent resin material and is fixed to the toilet seat 20. The reinforcing member 44 reinforces the toilet seat 20 of which the rigidity is reduced by forming the thin portion 23. The biological sensor 42 is mounted to the reinforcing member 44. The reinforcing member 44 includes a case part 45 to which the biological sensor 42 is mounted, and the protrusion 46 that protrudes from the case part 45 toward the recessed portion 24.

The case part 45 is box-like; and the biological sensor 42 is mounted inside the case part 45. As shown in FIGS. 5 and 6, the case part 45 is larger than the maximum diameter D of the thin portion 23 (the recessed portion 24) and smaller than the dimension between parallel heater wires 30 adhered to the back surface 22a of the thick portion 22.

The reinforcing member 44 is fixed to the toilet seat 20 so that the case part 45 is at a position separated from the reflected light Lt2 and the irradiated light Lt1 of the biological sensor 42. Specifically, a front surface 45a of the case part 45 of the reinforcing member 44 is bonded to the back surface 22a of the thick portion 22 by a sealing member 48 that is adhesive and waterproof. The sealing member 48 is, for example, a waterproof double-sided tape or adhesive. The reflected light Lt2 and the irradiated light Lt1 of the biological sensor 42 passes through the thin portion 23 of the seating part 21 and is not interfered with by the thick portion 22. Accordingly, the attenuation of the irradiated light Lt1 and the reflected light Lt2 by the sealing member 48 located at the thick portion 22 can be suppressed.

The sealing member 48 is positioned between the reinforcing member 44 and the seating part 21. Specifically, the sealing member 48 bonds the front surface 45a of the case part 45 to the back surface 22a of the thick portion 22 to surround the periphery of the recessed portion 24. Thereby, even if the thin portion 23 is damaged and water penetrates into the recessed portion 24, the penetration of the water from the recessed portion 24 into the toilet seat 20 interior can be suppressed by the sealing member 48. In other words, the sealing member 48 has an adhering function of adhering the reinforcing member 44 to the seating part 21, and a waterproofing function of suppressing the penetration of water into the toilet seat 20 interior.

The protrusion 46 protrudes from the front surface 45a of the case part 45 toward the thin portion 23. The protrusion 46 is positioned inside the recessed portion 24 in the state in which the reinforcing member 44 is fixed to the seating part 21. The protrusion 46 is transparent and transmits the reflected light Lt2 and the irradiated light Lt1 of the biological sensor 42. The reinforcing member 44 is easily aligned by inserting the protrusion 46 into the recessed portion 24.

The protrusion 46 reinforces the thin portion 23 of the seating part 21. Specifically, the protrusion 46 contacts the back surface 23a of the thin portion 23 and the circumferential wall surface 24a of the recessed portion 24 when, for example, the seating part 21 is deflected by the body weight of the user U seated on the toilet seat 20. Also, the case part 45 contacts the thick portion 22 at the periphery of the recessed portion 24. Thereby, the reinforcing member 44 suppresses the deflection of the periphery of the thin portion 23.

As shown in FIG. 6, a height dimension E2 of the protrusion 46 is less than the depth dimension E1 of the recessed portion 24 (E2<E1). Thereby, the reinforcing member 44 is fixed to the seating part 21 so that the gap S2 is formed between the front surface 46a of the protrusion 46 and the back surface 23a of the thin portion 23. The dimension S2a of the gap S2 is set by considering the manufacturing tolerances of the seating part 21 and/or the reinforcing member 44.

Thereby, when the protrusion 46 of the reinforcing member 44 is inserted into the recessed portion 24, the front surface 45a of the case part 45 can contact the back surface 22a of the thick portion 22 before the front surface 46a of the protrusion 46 contacts the back surface 23a of the thin portion 23. Accordingly, the reinforcing member 44 can be reliably fixed to the back surface 22a of the thick portion 22 by the sealing member 48.

The toilet seat device 10 according to the embodiment has the configuration described above; and the detection of the biological information by the biological sensor 42 included in the toilet seat device 10 will now be described.

For example, when electrical power is supplied from a power supply, the biological sensor 42 is constantly in the on-state in which the biological sensor 42 can detect. The biological sensor 42 is not limited thereto; the biological sensor 42 may be set to the on-state when the user U is detected by a human body detection sensor (not illustrated) detecting the user U approaching the toilet device 2 or by a seating sensor (not illustrated) detecting the user U seated on the toilet seat 20.

When the user U is seated on the toilet seat 20 as shown in FIG. 3, the buttocks vicinity that is below the center-of-gravity position G is compressed. For example, when the biological sensor 42 detects the biological information of the user U at this position, the blood flow inside the compressed buttocks is detected; therefore, the biological information may not be able to detect accurately.

Therefore, as shown in FIGS. 3 and 4, the biological sensor 42 is located frontward of the center-of-gravity position G of the user U seated on the toilet seat 20 and detects the blood flow inside the thigh portion U1 of the user U where the compression is small. In other words, the biological sensor 42 is located in the toilet seat 20 to be positioned below the thigh portion U1 of the user U seated on the toilet seat 20. Thereby, the biological sensor 42 can detect the biological information of the user U with high accuracy.

Here, in conventional art (JP-A 2020-39852 (Kokai)) described above, the vibration due to the pulse wave of the user seated on the toilet seat is detected. However, there is a possibility that such a pulse wave sensor may misdetect the body movement of the user; therefore, the pulse wave may not be able to detect with high accuracy.

Also, for example, when an opening and/or a sensor window is provided in the seating part of the toilet seat as in conventional art (JP-A 2017-6183 (Kokai)) described above, a joint of the opening and/or the sensor window is formed in the front surface of the toilet seat; therefore, the appearance of the toilet seat may be degraded. Also, the user U may feel discomfort when seated on the toilet seat 20 due to the joint contacting the skin.

A pulse wave sensor described in JP-A 2017-6183 (Kokai) measures the pulse wave by using red, blue, and green visible light. When such visible light is used, the biological information of the user U may not be able to detect with high accuracy when, for example, the subcutaneous fat of the user U seated on the toilet seat 20 is thick.

Therefore, the optical reflective sensor that is used by the biological sensor 42 according to the embodiment to detect the light reflected by the blood flow of the user U is a laser reflective sensor that uses infrared. Thereby, the biological sensor 42 can reduce the noise due to the body movement of the user U seated on the toilet seat 20.

Because the biological sensor 42 is a laser reflective sensor, the effects of the subcutaneous fat of the thigh portion U1 of the user U seated on the toilet seat 20 can be reduced. Accordingly, the biological information of the user U seated on the toilet seat 20 can be measured with high accuracy.

The biological sensor 42 is positioned below the thin portion 23 of the seating part 21 and is mounted to the reinforcing member 44. The thin portion 23 has a thickness that can transmit the reflected light Lt2 and the irradiated light Lt1 of the biological sensor 42. The thin portion 23 and the thick portion 22 are formed as a continuous body in the seating part 21. Thereby, the thin portion 23 of the seating part 21 is not visible from the front surface 21a side. In other words, the front surface 21a of the seating part 21 has a smooth planar shape without a joint; the design quality of the toilet seat 20 can be improved; and degradation of the sitting comfort can be suppressed.

The reinforcing member 44 that reinforces the periphery of the thin portion 23 is located below the thin portion 23. The reinforcing member 44 is larger than the thin portion 23 when viewed in plan. By positioning the protrusion 46 of the reinforcing member 44 in the recessed portion 24, the protrusion 46 contacts the circumferential wall surface 24a of the recessed portion 24 and the back surface 23a of the thin portion 23 when the seating part 21 is deflected. The deflection of the periphery of the thin portion 23 when the user U is seated on the toilet seat 20 can be reduced thereby.

The biological sensor 42 transmits the detection signal that is detected toward the controller 50. From the detection signal, the controller 50 measures and analyzes, for example, vital signs such as the pulse rate, the pulse rate variability, the blood flow, and the like, the fitness level, stress, the body water content, etc. Then, the controller 50 causes the display part 60a of the remote control 60 and/or the display part 65a of the portable terminal 65 to display the measured values and the analysis values. Other than the remote control 60 and the portable terminal 65, the controller 50 also may cause the display part of a PC terminal that is monitored in a hospital, a care facility, etc., to display the measured values and/or the analysis values. The controller 50 may monitor the measured values and/or the analysis values for each individual by identifying multiple users U. Thereby, the users U can be aware of their own health condition from past to present.

Mounting forms of the biological unit 40 to the seating part 21 will now be described with reference to FIGS. 9A to 9D.

Figure 9A:
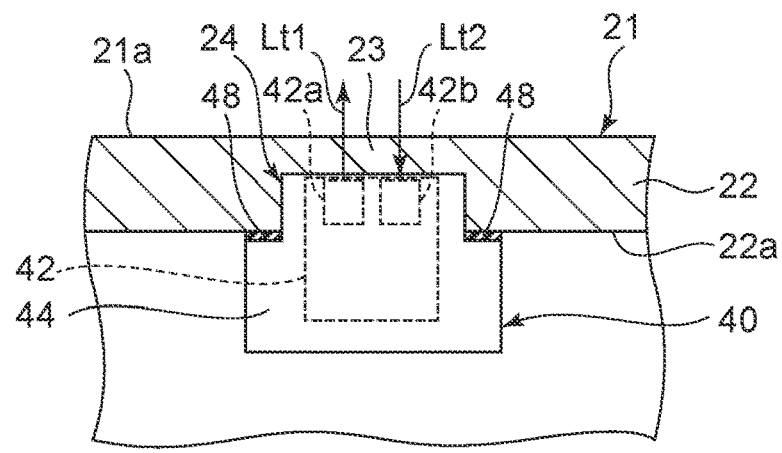
FIGS. 9A to 9D are explanatory drawings showing simplified mounting forms of the reinforcing member mounted to the toilet seat.
Figure 9B:
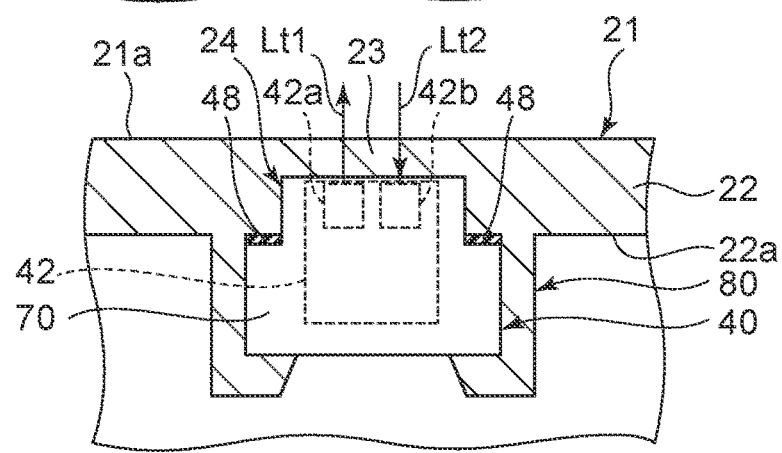
Figure 9C:
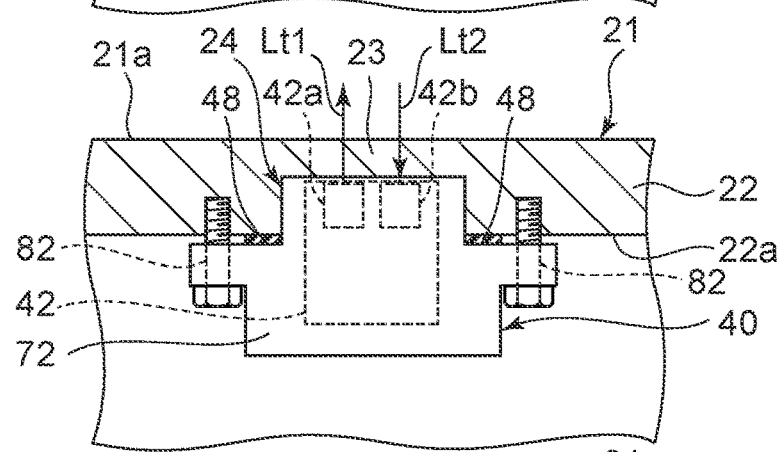
Figure 9D:
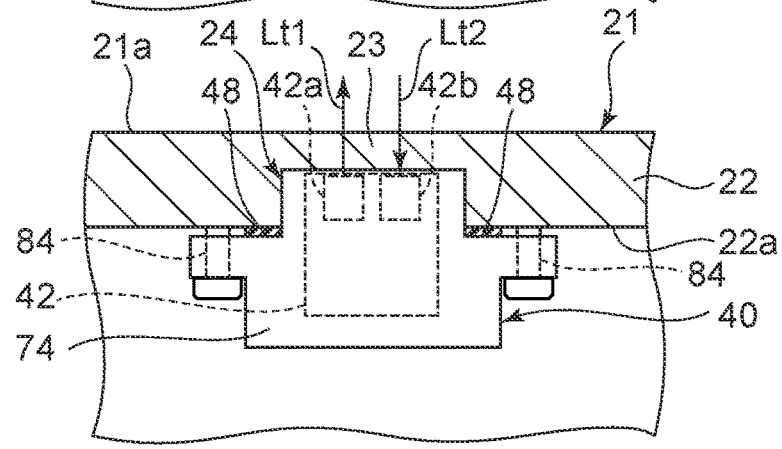

FIGS. 9A to 9D are explanatory drawings showing simplified mounting forms of the reinforcing member mounted to the toilet seat. FIG. 9A is an explanatory drawing showing a simplified mounting form of the reinforcing member 44 according to the embodiment described above. FIG. 9B is an explanatory drawing showing a simplified mounting form of a reinforcing member 70 according to a first modification. FIG. 9C is an explanatory drawing showing a simplified mounting form of a reinforcing member 72 according to a second modification. FIG. 9D is an explanatory drawing showing a simplified mounting form of a reinforcing member 74 according to a third modification.

As shown in FIG. 9A, the sealing member 48 adheres the reinforcing member 44 to the seating part 21 at a position separated from the light rays of the reflected light Lt2 and the irradiated light Lt1 of the biological sensor 42. Specifically, the sealing member 48 adheres the reinforcing member 44 to the back surface 22*a* of the thick portion 22 of the toilet seat 20. The attenuation of the reflected light Lt2 and/or the irradiated light Lt1 of the biological sensor 42 can be suppressed thereby.

The sealing member 48 is waterproof and is located between the reinforcing member 44 and the thick portion 22 to surround the periphery of the recessed portion 24. Thereby, even if the thin portion 23 is damaged and water penetrates into the recessed portion 24, the penetration of the water into the toilet seat 20 interior can be suppressed by the sealing member 48.

As in the first modification shown in FIG. 9B, the toilet seat 20 may further include a mating part 80 to which the reinforcing member 70 is mated. In other words, the reinforcing member 70 is bonded to the back surface 22*a* of the seating part 21, and is fixed to the toilet seat 20 by mating with the mating part 80 included in the toilet seat 20.

The reinforcing member 70 is adhered to the seating part 21 by the sealing member 48. Movement (misalignment) of the reinforcing member 70 inside the mating part 80 can be suppressed thereby. As a result, the light rays of the reflected light Lt2 and the irradiated light Lt1 of the biological sensor 42 are stable without shaking or moving; therefore, the effects on the detection accuracy of the biological sensor 42 can be suppressed. The mating part 80 extends from the thick portion 22 of the seating part 21 downward (toward the bottom surface part 25) and supports the reinforcing member 70 from below. Therefore, even if the reinforcing member 70 is detached from the seating part 21, the mating part 80 can prevent the reinforcing member 70 (the biological unit) from falling.

As in the second modification shown in FIG. 9C, the reinforcing member 72 may be fixed by fastening to the thick portion 22 of the seating part 21 by using a screw 82. As in the third modification shown in FIG. 9D, the reinforcing member 74 may be fixed by fusing to the thick portion 22 of the seating part 21 by using a pin 84 and thermal caulking. According to the second and third modifications, in addition to the screw 82 and/or the pin 84, the reinforcing members 72 and 74 are fixed to the seating part 21 by the sealing member 48 that is adhesive. However, according to the second and third modifications, the sealing member 48 may be provided as necessary; and a sealing member (e.g., an O-ring) that has only a waterproofing function may be used instead of the sealing member 48.

In examples according to embodiments described above, the seating part 21 includes two biological units 40 separated from each other in the lateral direction. However, the invention is not limited thereto; for example, one, three, or more biological units 40 may be included.

In examples according to embodiments described above, the biological sensor 42 is mounted to the reinforcing member 44. However, the invention is not limited thereto; for example, the biological sensor may be mounted to the bottom surface part and/or the seating part of the toilet seat.

In examples according to embodiments described above, the reinforcing member 44 is fixed to the thick portion 22. However, the invention is not limited thereto; for example, the reinforcing member may be fixed to the circumferential wall surface 24*a* of the recessed portion 24 and/or the back surface 23*a* of the thin portion 23 at a position separated from the light rays of the reflected light and the irradiated light of the biological sensor.

In examples according to embodiments described above, the sealing member 48 has both an adhering function and a waterproofing function. However, the invention is not limited thereto; for example, a sealing member that has only a waterproofing function and a bonding member such as double-sided tape, an adhesive, or the like may be provided separately. For example, an O-ring may be located between the protrusion 46 and the circumferential wall surface 24*a* of the recessed portion 24 as a sealing member; and the reinforcing member may be adhered to the seating part at another location.

In examples according to embodiments described above, the thin portion 23 is circular. However, the invention is not limited thereto; for example, the thin portion may have any shape such as rectangular, etc. This is similar for the protrusion 46 of the reinforcing member 44 as well.

For example, the following aspects may be considered to be toilet seat devices based on embodiments described above.

A first aspect is a toilet seat device that includes: a toilet seat that is formed of a resin material, includes a seating part on which a user is seated, and includes a bottom surface part facing the seating part; and a biological sensor that is of an optical type, is positioned inside the toilet seat, and detects biological information of the user seated on the seating part, wherein the seating part includes a thick portion and a thin portion, the thin portion is thinner than the thick portion, the biological sensor is located at a back surface side of the thin portion, the thick portion and the thin portion are formed as a continuous body, and the thin portion has a thickness that can transmit irradiated light irradiated from the biological sensor and reflected light reflected from the user seated on the seating part.

According to the first aspect, it is unnecessary to provide an opening and/or a sensor window that transmits the reflected light and/or the irradiated light of the biological sensor in the front surface of the toilet seat; therefore, the degradation of the design quality can be suppressed, and the biological information of the user seated on the toilet seat can be detected.

A second aspect is the toilet seat device of the first aspect, and includes a reinforcing member that is transparent, is fixed to the toilet seat between the thin portion and the biological sensor, and reinforces the toilet seat.

According to the second aspect, the thin portion that transmits the reflected light and/or the irradiated light of the biological sensor is a part that has decreased rigidity and easily deflects due to the body weight of the user seated on the toilet seat. Therefore, by providing the transparent reinforcing member at the thin portion, the strength and durability of the thin portion and the periphery of the thin portion can be ensured.

A third aspect is the toilet seat device of the second aspect, wherein the reinforcing member is fixed to the toilet seat at a position separated from the reflected light and the irradiated light of the biological sensor.

According to the third aspect, light may be absorbed and attenuated by a fixing part (e.g., double-sided tape, an adhesive, etc.) if the fixing part is located in a region that transmits the light rays of the irradiated light and/or the reflected light; therefore, the detection performance of the biological information may degrade. Therefore, by providing the fixing part of the reinforcing member in a region that does not transmit the irradiated light or the reflected light, the degradation of the detection performance of the biological sensor can be suppressed.

A fourth aspect is the toilet seat device of the third aspect, wherein the reinforcing member is fixed to the thick portion.

According to the fourth aspect, the reinforcing member is fixed to the thick portion; therefore, the size of the thin portion can have the minimum surface area for transmitting the irradiated light and/or the reflected light. Accordingly, the reduction of the rigidity of the toilet seat can be suppressed; the reinforcing member can be securely fixed to the thick portion; and the strength of the toilet seat can be further increased by the reinforcing member.

A fifth aspect is the toilet seat device of the third or fourth aspects, wherein the reinforcing member is fixed to form a gap between the reinforcing member and the back surface of the thin portion.

According to the fifth aspect, even when there is a dimension error of the toilet seat and/or the reinforcing member, the fixation of the reinforcing member can be prevented from being weakened by the back surface of the thin portion and the front surface of the reinforcing member abutting when fixing the reinforcing member.

A sixth aspect is the toilet seat device of the fifth aspect, wherein the dimension between the front surface of the biological sensor and the back surface of the reinforcing member is less than the dimension between the back surface of the thin portion and the front surface of the reinforcing member.

According to the sixth aspect, the attenuation of the reflected light and the irradiated light of the biological sensor can be suppressed by reducing the dimension between the front surface of the biological sensor and the back surface of the reinforcing member.

A seventh aspect is the toilet seat device of any one aspect of the second to sixth aspects that includes a sealing member located between the reinforcing member and the seating part to suppress the penetration of water into the toilet seat.

According to the seventh aspect, even if the thin portion is damaged, the penetration of the water into the toilet seat interior can be suppressed by the sealing member.

An eighth aspect is the toilet seat device of any one aspect of the second to seventh aspects, wherein the reinforcing member is bonded to the back surface of the seating part and is fixed to the toilet seat by mating with a mating part included in the toilet seat.

According to the eighth aspect, the reinforcing member can be accurately aligned by bonding to the seating part. The detection of the biological sensor can be stabilized thereby. Also, even if the reinforcing member is detached by deflection of the toilet seat, etc., the mating part can prevent the reinforcing member from falling.

A ninth aspect is the toilet seat device of any one aspect of the first to eighth aspects, wherein the maximum diameter of the thin portion is not more than 12 mm.

According to the ninth aspect, the reduction of the rigidity of the toilet seat can be suppressed because the maximum diameter of the thin portion is small. Also, even if the thin portion is damaged, the user can be prevented from inserting a finger into the toilet seat.

What is claimed is:

1. A toilet seat device, comprising:
    a toilet seat that is formed of a resin material and includes
        a seating part on which a user is seated, and
        a bottom surface part facing the seating part; and
    a biological sensor that is of an optical type, is positioned inside the toilet seat, and detects biological information of the user seated on the seating part,
    the seating part including a thick portion and a thin portion,
    the thin portion being thinner than the thick portion,
    the biological sensor being located at a back surface side of the thin portion,
    the thick portion and the thin portion being formed as a continuous body,
    the thin portion having a thickness that can transmit irradiated light irradiated from the biological sensor and reflected light reflected from the user seated on the seating part.

2. The device according to claim 1, wherein
    a reinforcing member reinforces the toilet seat and is fixed to the toilet seat between the thin portion and the biological sensor, and
    the reinforcing member is transparent.

3. The device according to claim 2, wherein
    the reinforcing member is fixed to the toilet seat at a position separated from the reflected light and the irradiated light of the biological sensor.

4. The device according to claim 3, wherein
    the reinforcing member is fixed to the thick portion.

5. The device according to claim 3, wherein
    the reinforcing member is fixed to form a gap between the reinforcing member and the back surface of the thin portion.

6. The device according to claim 5, wherein
    a dimension between a front surface of the biological sensor and a back surface of the reinforcing member is less than a dimension between the back surface of the thin portion and a front surface of the reinforcing member.

7. The device according to claim 2, wherein
    a sealing member is located between the reinforcing member and the seating part and suppresses a penetration of water into the toilet seat.

8. The device according to claim 2, wherein
    the reinforcing member is fixed to the toilet seat by being bonded to a back surface of the seating part and by mating with a mating part located in the toilet seat.

9. The device according to claim 1, wherein
    a maximum diameter of the thin portion is not more than 12 mm.

* * * * *